United States Patent [19]
Scholz

[11] Patent Number: 5,498,232
[45] Date of Patent: Mar. 12, 1996

[54] MICROCREPING OF FABRICS FOR ORTHOPEDIC CASTING TAPES

[75] Inventor: Matthew T. Scholz, Woodbury, Minn.

[73] Assignee: Minnesota Mining and Manufacturing Company, St. Paul, Minn.

[21] Appl. No.: 299,551

[22] Filed: Sep. 1, 1994

Related U.S. Application Data

[62] Division of Ser. No. 8,751, Jan. 25, 1993.

[51] Int. Cl.⁶ ..................................... A61F 13/00
[52] U.S. Cl. ..................................... 602/8; 602/6
[58] Field of Search ..................... 602/6, 8, 17, 18, 602/19, 20, 23

[56] References Cited

U.S. PATENT DOCUMENTS

| | | | |
|---|---|---|---|
| 2,765,513 | 10/1956 | Walton | 26/18.6 |
| 3,077,655 | 2/1963 | Runton | 26/18.5 |
| 3,260,778 | 7/1966 | Walton | 264/282 |
| 3,421,501 | 1/1969 | Beightol | 128/90 |
| 3,630,194 | 12/1971 | Boardman | 128/90 |
| 3,686,725 | 8/1972 | Nisbet et al. | 28/74 R |
| 3,787,272 | 1/1974 | Nisbet et al. | 161/89 |
| 3,793,686 | 2/1974 | Nisbet et al. | 28/75 R |
| 3,837,338 | 9/1974 | Chesky et al. | 128/156 |
| 3,908,644 | 9/1975 | Neinart et al. | 128/90 |
| 3,932,526 | 1/1976 | Koshar | 260/607 A |
| 3,972,323 | 8/1976 | Boricheski | 128/91 R |
| 4,041,581 | 8/1977 | Diggle, Jr. | 26/18.6 |
| 4,131,114 | 12/1978 | Kirkpatrick et al. | 128/90 |
| 4,134,397 | 1/1979 | Gianakakos et al. | 128/90 |
| 4,214,578 | 11/1980 | Gianakakos et al. | 128/90 |
| 4,376,438 | 3/1983 | Straube et al. | 128/90 |
| 4,411,262 | 10/1983 | von Bonin et al. | 128/90 |
| 4,433,680 | 2/1984 | Yoon | 128/90 |
| 4,441,262 | 4/1984 | Gazzoni | 34/57 D |
| 4,473,671 | 9/1984 | Green | 523/105 |
| 4,502,479 | 3/1985 | Garwood et al. | 128/90 |
| 4,609,578 | 9/1986 | Reed | 428/76 |
| 4,667,661 | 5/1987 | Scholz et al. | 128/90 |
| 4,668,563 | 5/1987 | Buese et al. | 428/230 |
| 4,704,113 | 11/1987 | Schoots | 602/45 |
| 4,705,840 | 11/1987 | Buckanin | 128/90 |
| 4,745,912 | 5/1988 | McMurray | 128/90 |
| 4,800,872 | 1/1989 | Buese et al. | 128/90 |
| 4,841,958 | 6/1989 | Ersfeld et al. | 128/90 |
| 4,940,047 | 7/1990 | Richter et al. | 128/90 |
| 4,947,839 | 8/1990 | Clark et al. | 128/90 |
| 4,984,566 | 1/1991 | Sekine et al. | 128/90 |
| 5,014,403 | 5/1991 | Buese | 28/170 |
| 5,027,804 | 7/1991 | Forsyth et al. | 128/90 |
| 5,060,349 | 10/1991 | Walton et al. | 264/282 |
| 5,088,484 | 2/1992 | Freeman | 602/900 |
| 5,169,698 | 12/1992 | Behjati et al. | 428/68 |
| 5,256,134 | 10/1993 | Ingham | 602/8 |
| 5,273,802 | 12/1993 | Scholz et al. | 428/76 |

FOREIGN PATENT DOCUMENTS 0407056  6/1990  European Pat. Off. ........ A61L 15/07

Primary Examiner—C. Fred Rosenbaum
Assistant Examiner—Michael L. Arness
Attorney, Agent, or Firm—Gary L. Griswold; Walter N. Kirn; F. Andrew Ubel

[57] ABSTRACT

The present invention provides an article, comprising: a fabric sheet which has been microcreped; and a curable resin coated onto the fabric sheet. The present invention involves microcreping or compacting a fabric sheet to impart stretchability and conformability to the fabric while minimizing undesirable recovery forces. Suitable fabrics for microcreping are fabrics which comprise fibers which are capable of first being mechanically compacted or "crimped" and then being set or annealed in the crimped, i.e., distorted, state. The article may be in the form of an orthopedic bandage and may optionally contain a plurality of microfiber fillers dispersed into the resin. The incorporation of microfiber fillers into the casting materials of the present invention adds substantially to the strength of the cured casting material, particularly when the fabric used therein is a non-fiberglass fabric, while not detracting from the handling properties of the uncured casting tape.

19 Claims, 2 Drawing Sheets

MICROCREPING OF FABRICS FOR ORTHOPEDIC CASTING TAPES

This is a division of application Ser. No. 08/008,751 filed Jan. 25, 1993.

FIELD OF THE INVENTION

This invention relates to sheet materials coated with a curable polymeric resin. More particularly, this invention relates to a curable resin coated sheet material useful in preparing an orthopedic bandage.

BACKGROUND OF THE INVENTION

Many different orthopedic casting materials have been developed for use in the immobilization of broken or otherwise injured body limbs. Some of the first casting materials developed for this purpose involve the use of plaster of Paris bandages consisting of a mesh fabric (e.g., cotton gauze) with plaster incorporated into the openings and onto the surface of the mesh fabric.

Plaster of Paris casts, however, have a number of attendant disadvantages, including a low strength-to-weight ratio, resulting in a finished cast which is very heavy and bulky. Furthermore, plaster of Paris casts typically disintegrate in water, thus making it necessary to avoid bathing, showering, or other activities involving contact with water. In addition, plaster of Paris casts are not air permeable, and thus do not allow for the circulation of air beneath the cast which greatly facilitates the evaporation and removal of moisture trapped between cast and skin. This often leads to skin maceration, irritation, or infection. Such disadvantages, as well as others, stimulated research in the orthopedic casting art for casting materials having improved properties over plaster of Paris.

A significant advancement in the art was achieved when polyisocyanate prepolymers were found to be useful in formulating a resin for orthopedic casting materials, as disclosed, for example, in U.S. Pat. No. 4,502,479 (Garwood et al.). U.S. Pat. No. 4,502,479 sets forth an orthopedic casting material comprising a knit fabric which is made from a high modulus fiber (e.g., fiberglass) impregnated with a polyisocyanate prepolymer resin such as polyurethane. Orthopedic casting materials made in accordance with U.S. Pat. No. 4,502,479 provide significant advancement over the plaster of Paris orthopedic casts, including a higher strength-to-weight ratio and greater air permeability. However, such orthopedic casting materials tend not to permit tactile manipulation or palpation of the fine bone structure beneath the cast to the extent possible when applying a plaster of Paris cast. In this regard, fiberglass knit materials are not as compressible as plaster, and tend to mask the fine structure of the bone as the cast is applied.

Although fiberglass fabrics are somewhat radiolucent they sometimes tend to mask the underlying bone structure to x-ray penetration. Oftentimes a fine mesh or a "shadow" can be seen on the x-ray image. This mesh, corresponding to the knitted fiberglass backing, obstructs the penetration of the x-rays and thereby obscures the fine detail of the underlying bone on the x-ray image. This is clearly undesirable.

Fiberglass backings have further disadvantages. Most, if not all, commercially available fiberglass casting bandages are comprised of filaments with diameters much larger than 3.5 microns (μm). While 3.5 μm fibers are considered by the scientific community to be non-respirable, there exists a sizable number of customers that have become concerned about the inhalation of fiberglass dust generated during cast removal.

Moreover, orthopedic casting materials involving knit fabrics such as fiberglass are somewhat expensive, and may be cost prohibitive for some users. In addition, fiberglass backings are comprised of fibers which have essentially no elongation. Because the fiber elongation is essentially nil, glass fabrics do not stretch unless they are constructed with very loose loops which can deform upon application of tension, thereby providing stretching of the fabric. Knitting with loosely formed chain stitches imparts extensibility by virtue of its system of interlocking knots and loose loops.

Like most knitted fabrics, fiberglass knits tend to curl or fray at a cut edge as the yarns are severed and adjacent loops unravel. Fraying and raveling produce unsightly ends and, in the case of an orthopedic cast, frayed ends may interfere with the formation of a smooth cast, and loose, frayed ends may be sharp and irritating after the resin thereon has cured. Accordingly, frayed edges are considered a distinct disadvantage in orthopedic casting tapes. Stretchy fiberglass fabrics which resist fraying are disclosed in U.S. Pat. No. 4,609,578 (Reed), the disclosure of which is incorporated by reference. Thus, it is well known that fraying of fiberglass knits at cut edges can be reduced by passing the fabric through a heat cycle which sets the yarns giving them new three-dimensional configurations based on their positions in the knit. When a fiberglass fabric which has been heat-set is cut, there is minimal fraying and when a segment of yarn is removed from the heat-set fabric and allowed to relax, it curls into the crimped shape in which it was held in the knit. Accordingly, at the site of a cut, the severed yarns have a tendency to remain in their looped or knotted configuration rather than to spring loose and cause fraying.

In processing extensible fiberglass fabrics according to U.S. Pat. No. 4,609,578 (Reed), a length of fabric is heat-set with essentially no tension. The fabric is often wound onto a cylindrical core so large batches can be processed at one time in a single oven. Care must be taken to avoid applying undue tension to the fabric during wind-up on the knitter which would distort the knots and loops. To prevent applying tension to the fabric during winding, the winding operation is preferably performed with a sag in the fabric as it is wound on the core. As is evident from the foregoing discussion, the entire process of knitting and heat-setting a fiberglass fabric is quite complex and expensive.

Alternatively, U.S. Pat. No. 5,014,403 (Buese) describes a method of making a stretchable orthopedic fiberglass casting tape by hitting an elastic yarn under tension into the fiberglass fabric in the length direction, releasing the tension from the elastic yarn to compact the fabric and removing the elastic yarn from the fabric. The casting bandage produced using this fabric, although stretchy, contains the aforementioned disadvantages of fiberglass casting bandages.

An example of an orthopedic bandage using a polyester fabric which is not a knitted fabric is disclosed in U.S. Pat. No. 3,972,323 (Boricheski). However, the orthopedic bandage disclosed in U.S. Pat. No. 3,972,323 involves the use of plaster of Paris, and thus is subject to the disadvantages outlined hereinabove for plaster of Paris orthopedic casts, including an inferior strength-to-weight ratio and poor air permeability. A second example of an orthopedic bandage using a polyester fabric which is not a knitted fabric is disclosed in U.S. Pat. No. 4,841,958 (Ersfeld et al.). However, because the polyester fabric backing disclosed in U.S. Pat. No. 4,841,958 causes the cast to have a somewhat lower strength and a lower rigidity than fiberglass casts, these casting materials require more layers of casting tape to achieve a weight bearing orthopedic cast.

U.S. Pat. No. 4,984,566 (Sekine et al.) discloses an orthopedic casting tape providing stretchability which comprises a knitted fibrous substrate impregnated with a water-curable synthetic resin wherein the substrate consists of synthetic organic fiber stretch yarn solely, in part stretch yarn and in pan artificial fibers or in pan stretch yarn and in part mixtures of natural and artificial fibers. The stretch yarns are preferably those in which the stretchability is conferred by providing spiral or zigzag patterns of the synthetic fibers and utilizing the thermal plasticity and shrinkage properties of the synthetic fibers which are non-elastomeric.

From the foregoing, it will be appreciated that what is needed in the an is an orthopedic casting material which has both the advantages of plaster of Paris, e.g., good moldability and palpability of the free bone structure, and the advantages of non-plaster of Paris materials, e.g., good strength-to-weight ratio and good air permeability. In this regard it would be a significant advancement in the an to provide such a combination of advantages without actually using plaster of Paris, thereby avoiding the inherent disadvantages of plaster of Paris outlined herein. It would be a further advancement in the art to provide such non-plaster of Paris orthopedic casting materials which have as good or better properties than the orthopedic casting materials of the prior art, and which can be made to be significantly less expensive, and therefore less cost prohibitive, than prior art orthopedic casting materials employing knitted fabrics such as fiberglass knits. Such orthopedic casting materials and methods for preparing the same are disclosed and claimed herein.

RELATED APPLICATIONS

Of related interest are the following U.S. Patent Applications, filed on Jan. 25, 1993 by the assignee of this invention: Microfiber Fillers for Orthopedic Casting Tapes—Ser. No. 08/008,755; Mechanically Compacted Fabrics for Orthopedic Casting Tapes—Ser. No. 08/008,161; Water Curable Resin Compositions—Ser. No. 08/008,743; Orthopedic Support Materials and Method—Ser. No. 08/008,678; and Fabric Backing for Orthopedic Support Materials—Ser. No. 08/009,923 which are herein incorporated by reference.

SUMMARY OF THE INVENTION

The present invention provides an article; comprising: a fabric sheet which has been microcreped; and a curable resin coated onto the fabric sheet. The article may be in the form of an orthopedic bandage and may optionally contain a microfiber filler associated with the resin. The article may also be in the form of a water-hardenable medical dressing capable of immobilizing and/or supporting a body part. This hardenable dressing can be used in tape, sheet, film, slab, or tubular form to prepare orthopedic casts, splints, braces, supports, protective shields, orthotics, and the like. Additionally, other constructions in prefabricated shapes can be used. As used herein the terms "orthopedic support material" or "orthopedic casting material" are used to encompass any of these forms of dressings, and "cast" or "support" are used to include any of these orthopedic support structures. The incorporation of microfiber fillers into the casting materials of the present invention adds substantially to the strength of the cured casting material, particularly when the fabric used therein is a non-fiberglass fabric, while not detracting from the handling properties of the uncured casting tape or bandage. The microcreped sheet imparts increased extensibility to the casting bandage.

DETAILED DESCRIPTION OF THE INVENTION

Figure 1:
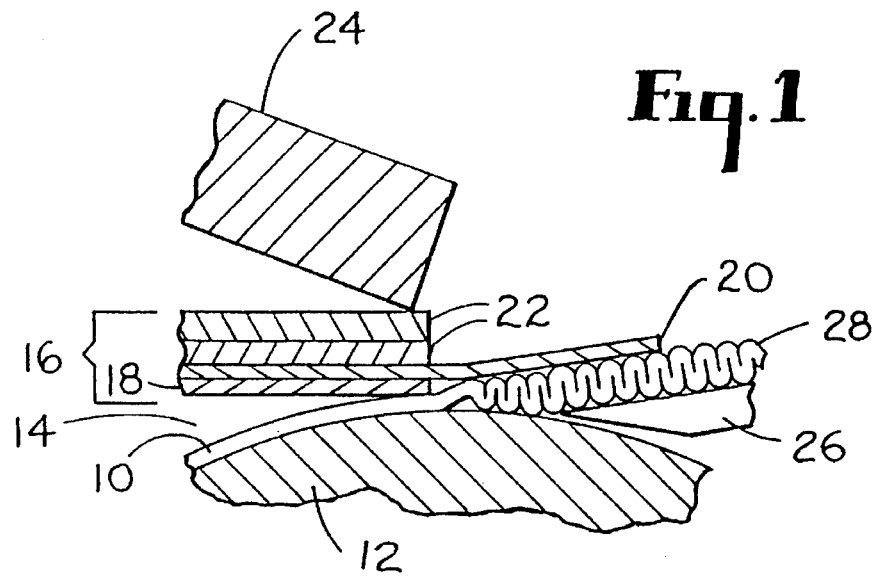
FIGS. 1, 2, and 3 illustrate variations of the Micrex process described herein.

The present invention relates to orthopedic casting materials and methods for preparing and using such orthopedic casting materials, wherein the materials comprise a backing or fabric which is impregnated with a curable liquid resin. In particular, the fabrics employed in the present invention have important characteristics and physical properties which allow the fabrics to be made highly extensible. At the same time, the orthopedic casting materials of the present invention are relatively inexpensive, thus providing a more economical alternative to the non-plaster of Paris orthopedic casting materials presently known in the art which employ knitted fabrics such as fiberglass fabrics.

One element of this invention is a flexible sheet upon which a curable resin can be coated to reinforce the sheet when the resin is cured thereon. The sheet is preferably porous such that the sheet is at least partially impregnated with the resin. Examples of suitable sheets are non-woven, woven, or knit fabrics comprised of organic natural or synthetic fibers or materials. The sheet may alternatively be referred to as the "scrim" or the "backing."

The present invention involves microcreping or compacting a fabric sheet to impart stretchability and conformability to the fabric while minimizing undesirable recovery forces. "Microcreping," as used herein, means mechanically compacting a fabric so that it has a smaller lengthwise dimension than it originally had. A "microcreped fabric," as used herein, is a fabric that has been mechanically compacted so that it has a smaller lengthwise dimension than it originally had. Suitable fabrics for microcreping are fabrics which comprise fibers which are capable of first being mechanically compacted or "crimped" and then being set or annealed in the crimped, i.e., distorted, state. Undesirable fabrics for microcreping include those fabrics which comprise fibers which are incapable of being so crimped. This is especially important when the uncrimpable fibers are oriented in the wale, length, or machine direction of the fabric. For example, glass fibers oriented in the wale, length, or machine direction of the fabric and fabrics made completely from glass Fibers are not desirable for use in the present invention. Fiberglass fabrics tend not to respond well to the microcreping process. Rather, the glass fibers tend to break and shatter when so compacted. Glass fiber may, however, be incorporated into a fabric such that the fabric would be suitable for microcreping. For example, the glass fibers could be incorporated into the fabric in the width or weft direction and thereby not be subjected to crimping during the microcreping process.

Suitable backings of the present invention include fabrics comprising: natural organic fibers; animal derived materials; naturally based organic polymer fibers; and synthetic polymer fibers. Suitable fibers for use in the fabric of the present invention include natural organic fibers such as: vegetable derived materials such as abaca, cotton, flax, hemp, jute, kapok, linen, ramie, and sisal; and animal derived materials such as wool, mohair, vicuna, other animal hairs, and silk. Presently preferred natural organic fibers include: cotton and wool. Cotton is presently most preferred.

Presently preferred polymer fibers for use in the fabric of the present invention include; naturally based organic polymers such as acetate, azlon, rayon, and triacetate; and synthetically prepared organic polymers such as acrylic, aramid, nylon, olefin (e.g., poly(1-butene), polyethylene, poly(3-methyl-1-butene), poly(1-pentene), polypropylene, and polystyrene), polyester, polytetrafluoroethylene, poly(vinyl alcohol), poly(vinyl chloride), and poly(vinylidine chloride). Presently preferred synthetic polymer fibers include: acrylic, nylon, polyethylene, polypropylene, polyester, and rayon. Presently most preferred synthetic polymer fibers include: nylon, polyester, and rayon.

The microcreping process may be done using a variety of fabric consauctions including knits, wovens, and nonwovens such as spun laced and hydroentangled fabrics. One preferred hydroentangled fabric is sold under the tradename "Sontara" 8043 (available from DuPont Co.). Suitable sheets for use in the present invention are described, for example, in U.S. Pat. Nos. 4,940,047; 4,984,566; and 4,841,958. Preferred non woven sheets are disclosed in U.S. Pat. No. 4,841,958 (Ersfeld et al.) which is herein incorporated by reference.

The microcreping process is a mechanical way to impart functional qualities to web structures. In one embodiment of the process, an untreated web (e.g., a fabric), supported by a main roll, is introduced into a converging passage, firmly gripped, and conveyed into the main treatment cavity where the microcreping process takes place. By adjustment of controls, varying amounts of residual compaction and crepe cross-section can be attained, depending upon the desired result and the characteristics of the material being treated. The treated web passes through a secondary passage between rigid and/or flexible retarders which control the uniformity and degree of compaction. Compaction is retained in the fabric by annealing the fibers in the compacted state. By "annealing" is meant the maintenance of the fiber at a specified temperature for a specific length of time and then cooling the fiber. This treatment removes internal stresses resulting from the previous microcreping operation effectively "setting" the fabric structure in a new preferred orientation. This can be done using dry heat (e.g., hot roll, infrared irradiation, convection oven, etc.) or steam. The choice of annealing method depends upon such factors as fabric weight, fiber type and process speed. One simple method to apply heat to the fabric is to pass the fabric over a heated roll. Alternatively, steam heat is preferred for some fabrics.

A microcreped fabric which has not been annealed may be employed in casting tapes of the present invention. It is presently believed that such fabrics will exhibit suitable extensibility, however, they likely will require greater care during processing (e.g., when applying resin thereto) to maintain the fabric's compacted state.

Two commercial microcreping processes are believed to be capable of treating fabrics of the present invention. One such process, discussed above, is commercialized by the Micrex Corporation of Walpole, Mass. (the "Micrex" process). A second such process is commercialized by the Tubular Textile Machinery Corporation of Lexington, N.C. (the "TTM" process). The TTM process is similar in principle to the Micrex process—although certain details are different. In the TTM process, the fabric is passed into the compacting zone over a feed roll and under a shoe. The fabric is then compacted or microcreped by contacting a lower compacting shoe and a retarding roll. Nevertheless, in both processes the fabric is subjected to a compaction force due to frictional retarders.

As depicted in FIG. 1, an untreated web 10, supported by a main roll 12, is introduced into a converging passage 14 between the main roll and a movable retarder 16. The movable retarder has a primary surface 18, a flexible retarder 20, and one or more back-up blades 22. The movable retarder is held against the untreated web using a pressure plate 24. The web passes through a secondary passage between the flexible retarder and a rigid retarder 26 and exits as a treated web 28.

Figure 2:
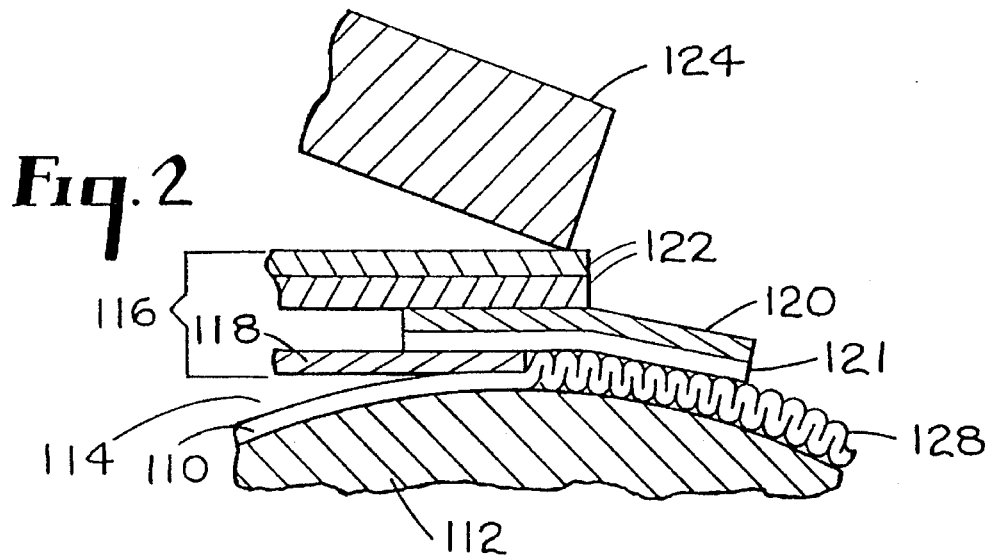

As depicted in FIG. 2, an untreated web 110, supported by a main roll 112, is introduced into a converging passage 114 between the main roll and a movable retarder 116. The movable retarder has a primary surface 118, a flexible retarder 120, a frictional retarder 121, and one or more back-up blades 122. The movable retarder is held against the untreated web using a pressure plate 124. The web passes through a secondary passage between the frictional retarder 121 and the main roll 112 and exits as a treated web 128.

Figure 3:
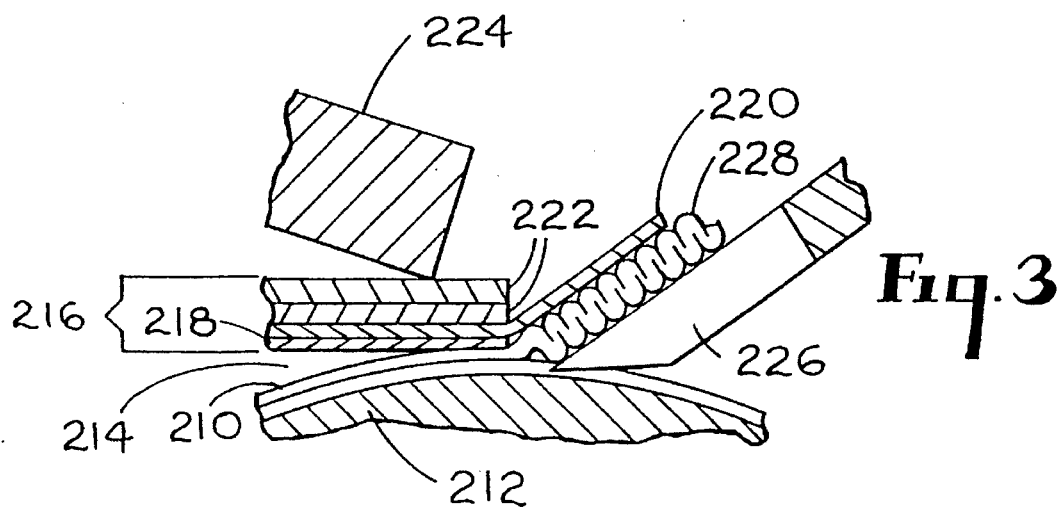

As depicted in FIG. 3, an untreated web 210, supported by a main roll 212, is introduced into a converging passage 214 between the main roll and a movable retarder 216. The movable retarder has a primary surface 218, a flexible retarder 220, and one or more back-up blades 222. The movable retarder is held against the untreated web using a pressure plate 224. The web passes through a secondary passage between the flexible retarder and a comb 226 and exits as a treated web 228.

Figure 4:
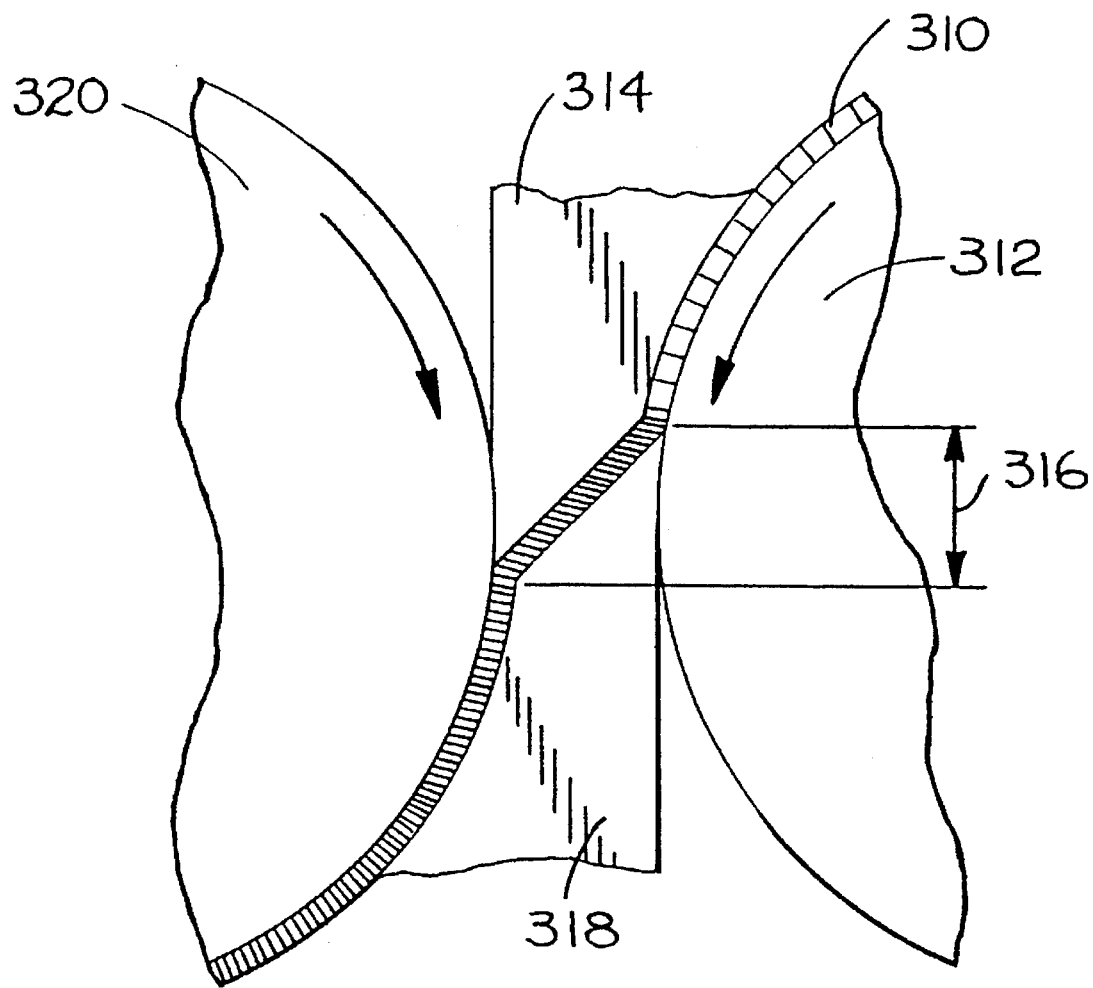
FIG. 4 illustrates an embodiment of the Tubular Textile Machinery process described herein.

As depicted in FIG. 4, an untreated web 310, supported by a feed roll 312, is introduced into a passage between an upper compacting shoe 314 and the feed roll. The web then passes into a compacting zone 316 between the upper compacting shoe and a lower compacting shoe 318. The web becomes compacted in this zone and exits through a passage between the lower compacting shoe and a retarding roll 320.

Suitable fabrics, after microcreping, have important characteristics and physical properties which allow the fabrics to be resin loaded to the extent needed to provide proper strength as an orthopedic casting material, while providing necessary porosity as well as improved extensibility leading to improved conformability, tactile manipulability, moldability, and palpability. Several important criteria for choosing a fabric which will provide the characteristics necessary for purposes of the present invention include: (1) lengthwise extensibility and conformability after microcreping, and the related characteristics of moldability, tactility, and palpability once the fabric has been resin impregnated; (2) resin loading capacity; and (3) porosity. It is important that each of these parameters be carefully controlled in providing fabrics which will successfully form orthopedic casting materials within the scope of the present invention.

Extensibility is important from the standpoint that the fabric must be extensible enough along its length, i.e., in the elongated direction, so that the resultant orthopedic casting material can be made to substantially conform to the body part to which it is applied. Materials which are not sufficiently extensible in the elongated direction do not conform well to the body part when wrapped therearound, often resulting in undesirable wrinkles or folds in the material. On the other hand, the extensibility of the fabric in the elongated direction should not be so high that the material is too stretchy, resulting in a material structure which may be deformed to the extent that resin holding capacity and porosity are substantially reduced.

For purposes of the present invention, the fabric, after microcreping, should have from about 10% to about 200% extensibility in the elongated direction when a 268 gram load or force is applied across a 1 cm section of the fabric, and preferably from about 25% to about 75% extensibility in the elongated direction when a 268 gram load or force is applied across a 1 cm section of the fabric, and more preferably from about 35% to about 55% extensibility in the elongated direction when a 268 gram load or force is applied across a 1 cm section of the fabric.

Although not nearly as critical, it is also desirable that the fabric employed have some extensibility along its width, i.e., in the direction transverse to the elongated direction. Thus although the fabric may have from 0% to 100% extensibility in the transverse direction, it is presently preferable to use a fabric having from about 1% to about 30% extensibility in the transverse direction when a 268 gram load or force is applied across a 1 cm section of the fabric. The microcreping process previously described generally only imparts extensibility in the elongated direction. However, it is anticipated that one might microcrepe a fabric twice, i.e., once in the elongated direction and a second time in the transverse direction, thereby imparting biaxial extensibility. Alternatively, both longitudinal and transverse microcreping may be imparted simultaneously, e.g., both longitudinal and transverse crimping may be accomplished prior to the annealing step. In addition, a fabric having width extensibility such as a knit can be microcreped to impart or increase the lengthwise extensibility while not significantly affecting the widthwise extensibility.

The fabrics of the present invention, after microcreping, although stretchable, are preferably not overly elastic or resilient. Fabrics which are overly elastic, when used as backings for orthopedic bandages, tend to cause undesirable constriction forces around the wrapped limb or body part. Thus, once the resin impregnated fabric has been stretched and applied around a body part, the stretched material preferably maintains its shape and does not resort back to its unstretched position.

The resin loading capacity or ability of the fabric to hold resin is important from the standpoint of providing an orthopedic casting material which has sufficient strength to efficaciously immobilize a body part. The surface structure of the fabric, including the fibers, interstices, and apertures, is very important in providing proper resin loading for purposes of the present invention. In this regard, the interstices between the fibers of each fiber bundle must provide sufficient volume or space to hold an adequate amount of resin within the fiber bundle to provide the strength necessary; while at the same time, the apertures between fiber bundles preferably remain sufficiently unoccluded such that adequate porosity is preserved once the resin is applied. Thus, the interstices between fibers are important in providing the necessary resin loading capacity, while the apertures are important in providing the necessary porosity for the finished cast. However, a balancing of various parameters is needed to achieve both proper resin loading and porosity. The fabric should have preferably between about 6 and 90 openings (i.e., apertures) per square cm, more preferably between about 10 and 50 openings per square cm, and most preferably between about 20 and 40 openings per square cm.

The microcreping process may impart extensibility to the fabric by several different mechanisms. For example, for knit fabrics the microcreping process may mechanically compact the loops of the knit without further distorting fiber bundles. Typically, when a fabric is knitted the inside surfaces of two adjacent rows of loops are in contact or nearly in contact. This contact is the result of the fabric being under tension while the knit loops are being formed. Each successive row of loops is, in effect, formed against the preceding row of loops. The microcreping process of the instant invention appears to impart fabric compaction by overlapping adjacent rows of loops or the loops may be deformed in the plane of the fabric in either an overlapping or non-overlapping position and then optionally, and preferably, setting or annealing the fabric in the compacted form. Extensibility is imparted to the fabric due to the overlap of the rows. When tension is again applied to the fabric, the loops can return to their original "contacting" position, i.e., the position they occupied when originally knit.

In contrast, woven or non-woven fabrics may be microcreped in a slightly different manner. First, it is necessary to differentiate between fabrics which are cut on or produced on the bias and those which are cut at an angle to the fabric bias. For fabrics which are cut on the bias, the microcreping process appears to distort fiber bundles (i.e., crimp the fibers) which run in the machine direction and collapse the aperatures. A fiber bundle which runs in the machine direction is crimped either: inplane (i.e., into adjacent aperture openings); or out of the plane of the fabric (thereby increasing fabric thickness). The crimped fiber bundles may then be set or annealed in their compacted form. When tension is later applied to the treated fabric the crimped fiber bundles can be, "straightened" into their original uncrimped form thereby lengthening the fabric. At low tensions, the fiber bundles may resist this straightening thereby causing the fabric to exhibit rebound. For fabrics which are cut at an angle to the bias, the microcreping process appears to distort the shape of the apertures. Fabrics that once had rectangular or square apertures, oriented at an angle to the machine direction, have distorted diamond shaped apertures after microcreping. Similarly, fabrics that once had round apertures have distorted oval shaped apertures after microcreping. In addition, some in-plane or out-of-plane fiber bundle crimping may take place. In cases where out of plane compacting occurs it is desirable to avoid too extensive a result which would significantly increase the fabric thickness. The thickness of the fabric is not only optimized in view of the resin loading and resin layer thickness, but also in view of the number of layers in a cast. That is, the thickness of the fabric is balanced against the resin load, resin layer thickness, and number of layers of tape in a cast. Typically, a cast consists of about 4–12 layers of overlapping wraps of tape, preferably about 4–5 layers in nonweight-bearing uses and 8–12 layers in weight bearing areas such as the heel. Thus, a sufficient amount of curable resin is applied in these few layers to achieve the desired ultimate cast strength and rigidity. The appropriate amount of curable resin can be impregnated into the backing of the present invention using fabrics having a thickness of about 0.5–1.5 mm. Preferably, the fabrics are thin, i.e., having a thickness of less than about 1.3 mm. More preferably, the fabrics of the present invention have a thickness of about 0.76–1.0 mm measured using an Ames Gauge Co. (Walthanm, Mass.) 202 thickness gauge with a 2.54 cm diameter contact.

Suitable fabrics, after microcreping, are compacted to between about 10 and 65 percent of their original dimension in the lengthwise direction. More preferably, the fabric is compacted to between about 20 and 60 percent of its original dimension in the lengthwise direction, and most preferably, the fabric is compacted to between about 30 and 50 percent of its original dimension in the lengthwise direction.

It should be noted that the extent of microcreping need not be uniform across the width of the fabric. Patterns or decorative designs may be employed using differential compaction delivered by properly designed retarders. In addition, the fabrics of the present invention may be dyed or printed for aesthetic or functional purposes.

The curable resins useful in this invention are resins which can be used to coat a sheet material and which can then be cured to reinforce the sheet material. The resin is curable to a crosslinked thermoset state. The preferred curable resins are fluids, i.e., compositions having viscosities between about 5 Pa s and about 500 Pa s, preferably about 10 Pa s to about 100 Pa s.

The resin used in the casting material of the invention is preferably any curable resin which will satisfy the functional requirements of an orthopedic cast. Obviously, the resin must be nontoxic in the sense that it does not give off significant amounts of toxic vapors during curing which may be harmful to either the patient or the person applying the cast and also that it does not cause skin irritation either by chemical irritation or the generation of excessive heat during cure. Furthermore, the resin must be sufficiently reactive with the curing agent to insure rapid hardening of the cast once it is applied but not so reactive that it does not allow sufficient working time to apply and shape the cast. Initially, the casting material must be pliable and formable and should adhere to itself. Then in a short time following completion of cast application, it should become rigid or, at least, semi-rigid, and strong to support loads and stresses to which the cast is subjected by the activities of the wearer. Thus, the material must undergo a change of state from a fluid-like condition to a solid condition in a matter of minutes.

The preferred resins are those cured with water. Presently preferred are urethane resins cured by the reaction of a polyisocyanate and a polyol such as those disclosed in U.S. Pat. No. 4,131,114. A number of classes of water-curable resins known in the art are suitable, including polyurethanes, cyanoacrylate esters, and, when combined with moisture sensitive catalysts, epoxy resins and prepolymers terminated at their ends with trialkoxy- or trihalo-silane groups. For example, U.S. Pat. No. 3,932,526 discloses that 1,1-bis(perfluoromethylsulfonyl)-2-aryl ethylenes cause epoxy resins containing traces of moisture to become polymerized.

Resin systems other that those which are water-curable may be used, although the use of water to activate the hardening of an orthopedic casting tape is most convenient, safe and familiar to orthopedic surgeons and medical casting personnel. Resin systems such as that disclosed in U.S. Pat. No. 3,908,644 in which a bandage is impregnated with difunctional acrylates or methacrylates, such as the bismethacrylate ester derived from the condensation of glycidyl methacrylate and bisphenol A (4,4'-isopropylidenediphenol) are suitable. The resin is hardened upon wetting with solutions of a tertiary amine and an organic peroxide. Also, the water may contain a catalyst. For example, U.S. Pat. No. 3,630,194 proposes an orthopedic tape impregnated with acrylamide monomers whose polymerization is initiated by dipping the bandage in an aqueous solution of oxidizing and reducing agents (known in the art as a redox initiator system). The strength, rigidity and rate of hardening of such a bandage is subjected to the factors disclosed herein.

Some presently more preferred preferred resins for use in the present invention are water-curable, isocyanate-functional prepolymers. Suitable systems of this type are disclosed, for example, in U.S. Pat. Nos. 4,411,262, and 4,502,479. Presently more preferred resin systems are disclosed in U.S. Pat. No. 4,667,661 and U.S. patent application Ser. No. 07/376,421 which is herein incorporated by reference. The following disclosure relates primarily to the preferred embodiment of the invention wherein water-curable isocyanate-functional prepolymers are employed as the curable resin. A water-curable isocyanate-functional prepolymer as used herein means a prepolymer derived from polyisocyanate, preferably aromatic, and a reactive hydrogen compound or oligomer. The prepolymer has sufficient isocyanate-functionality to cure upon exposure to water, e.g., moisture vapor, or preferably liquid water.

It is preferred to coat the resin onto the fabric as a polyisocyanate prepolymer formed by the reaction of an isocyanate and a polyol. It is preferred to use an isocyanate which has low volatility such as diphenylmethane diisocyanate (MDI) rather than a more volatile material such as toluene diisocyanate (TDI). Suitable isocyanates include 2,4-toluene diisocyanate, 2,6-toluene diisocyanate, mixture of these isomers, 4,4'-diphenylmethane diisocyanate, 2,4'-diphenylmethane diisocyanate, mixture of these isomers together with possible small quantifies of 2,2'-diphenylmethane diisocyanate (typical of commercially available diphenylmethane diisocyanate), and aromatic polyisocyanates and their mixture such as are derived from phosgenation of the condensation product of aniline and formaldehyde. Typical polyols for use in the prepolymer system include polypropylene ether glycols (available from Arco Chemical Co. under the trade name Arcol™ PPG and from BASF Wyandotte under the trade name Pluracol™), polytetramethylene ether glycols (Polymeg™ from the Quaker Oats Co.), polycaprolactone diols (Niax™ PCP series of polyols from Union Carbide), and polyester polyols (hydroxyl terminated polyesters obtained from esterification of dicarboxylic acids and diols such as the Rucoflex™ polyols available from Ruco division, Hooker Chemical Co.). By using high molecular weight polyols, the rigidity of the cured resin can be reduced.

An example of a resin useful in the casting material of the invention uses an isocyanate known as Isonate™ 2143L available from the Upjohn Company (a mixture containing about 73% of MDI) and a polypropylene oxide polyol from Union Carbide known as Niax™ PPG725. To prolong the shelf life of the material, it is preferred to include from 0.01 to 1.0 percent by weight of benzoyl chloride or another suitable stabilizer.

The reactivity of the resin once it is exposed to the water curing agent can be controlled by the use of a proper catalyst. The reactivity must not be so great that: (1) a hard film quickly forms on the resin surface preventing further penetration of the water into the bulk of the resin; or (2) the cast becomes rigid before the application and shaping is complete. Good results have been achieved using 4-[2-[1-methyl-2-(4-morpholinyl)ethoxy]ethyl]morpholine (MEMPE) prepared as described in U.S. Pat. No. 4,705,840, the disclosure of which is incorporated by reference, at a concentration of about 0.05 to about 5 percent by weight.

Foaming of the resin should be minimized since it reduces the porosity of the cast and its overall strength. Foaming occurs because carbon dioxide is released when water reacts with isocyanate groups. One way to minimize foaming is to reduce the concentration of isocyanate groups in the prepolymer. However, to have reactivity, workability, and ultimate strength, an adequate concentration of isocyanate groups is necessary. Although foaming is less at low resin contents, adequate resin content is required for desirable cast characteristics such as strength and resistance to peeling. The most satisfactory method of minimizing foaming is to add a foam suppressor such as silicone Antifoam A (Dow Corning), or Antifoam 1400 silicone fluid (Dow Corning) to the resin. It is especially preferred to use a silicone liquid such as Dow Corning Anti-foam 1400 at a concentration of about 0.05 to 1.0 percent by weight. Water-curable resins containing a stable dispersion of hydrophobic polymeric particles, such as disclosed in U.S. patent application Ser. No. 07/376,421 and laid open as European Published Patent Application EPO 0 407 056, may also be used to reduce foaming.

Also included as presently more preferred resins in the instant invention are non-isocyanate resins such as water reactive liquid organometallic compounds. These resins are especially preferred as an alternative to isocyanate resin systems for those persons who have allergic reactions to isocyanate materials. Water-curable resin compositions suitable for use in an orthopedic cast consist of a water-reactive liquid organometallic compound and an organic polymer. The organometallic compound is a compound of the formula $(R^1O)_xMR^2_{(y-x)}$ wherein: each $R^1$ is independently a $C_1$–$C_{100}$ hydrocarbon group, optionally interrupted in the backbone by 1–50 nonperoxide —O—, —S—, —C(O)—, or —N— groups; each $R^2$ is independently selected from the group consisting of hydrogen and a $C_1$–$C_{100}$ hydrocarbon group, optionally interrupted in the backbone by 1–50 nonperoxide —O—, —S—, —C(O)—, or —N— groups; x is an integer between 1 and y, inclusive; y is the valence of M; and M is boron, aluminum, silicon, or titanium. The organic polymer is either an addition polymer or a condensation polymer. Addition polymers are preferably utilized as the organic polymer constituent Particularly useful addition polymers are those made from ethylenically unsaturated monomers. Commercially available monomers, from which such addition polymers can be formed, include but are not limited to, ethylene, isobutylene, 1-hexene, chlorotrifluoroethylene, vinylidene chloride, butadiene, isoprene, styrene, vinyl napthalene, ethyl acrylate, 2-ethylhexyl acrylate, tetrahydrofurfuryl acrylate, benzyl acrylate, poly(ethylene oxide)monoacrylate, heptafluorobutyl acrylate, acrylic acid, methyl methacrylate, 2-dimethylaminoethyl methacrylate, 3-methacryloxypropyltris(trimethylsiloxy)silane, isobutyl methacrylate, itaconic acid, vinyl acetate, vinyl stearate, N,N-dimethylacrylamide, tert-butyl acrylamide, acrylonitrile, isobutyl vinyl ether, vinyl pyrrolidinone, vinyl azlactone, glycidyl methacrylate, 2-isocyanatoethyl methacrylate, maleic anhydride, vinyl triethoxysilane, vinyl tris(2-methoxyethoxy)silane, and 3-(trimethoxysilyl)propyl methacrylate. Polymers bearing hydrolyzable functionality are preferred. An acidic or basic catalyst may be used to accelerate the water cure of these compositions. Strong acid catalysts are preferred.

Preferably, the scrims of the present invention are coated with a resin which incorporates microfiber fillers. These preferred orthopedic bandages enjoy many benefits, for example, resins which incorporate microfiber fillers exhibit: a dramatic increase in strength when coated on the backings of the present invention; an increased "early strength" upon curing; an improved durability and higher modulus; good and often better layer-to-layer lamination strength; a lower exotherm upon setting; and a lower effective resin cost compared to resins which do not incorporate such microfiber fillers. Casting bandages which employ the microfiber fillers and the backings of the present invention also have improved radiolucency compared to typical fiberglass bandages, i.e., the microfiber fillers do not superimpose a mesh shadow pattern on the image of the bone, thereby obscuring fine details of the bone. In addition, resin suspensions employing the microfiber fillers of the present invention exhibit generally very little increase in resin viscosity— thereby ensuring easy unwind of the casting bandage and good handling properties such as drapability.

A "microfiber filler" as used herein, is a filler which when incorporated into the casting tapes of the present invention provide the desired increase in strength while not adversely affecting the uncured resin suspension viscosity (thereby adversely affecting the drapability of the casting tape). The microfiber fillers useful in this invention are generally characterized as being short fibers having an aspect ratio greater than five to one. "Aspect ratio" as used herein, refers to the ratio of the fiber's length to its diameter. For fibers having an irregular or non-circular cross section, the "diameter" of the micro fiber shall be equal to the largest width across the microfiber. Blends of microfibers having different aspect ratios may be utilized in the casting tapes of the present invention. For purposes of this invention, when blends of microfibers are employed, the aspect ratio of the blend of microfibers refers to the mean aspect ratio. Preferred microfiber fillers or blends have an aspect ratio between 5:1 and 200:1. More preferably, the aspect ratio of the microfiber is between 5:1 and 50:1. Most preferably, the aspect ratio of the microfiber is between 10:1 and 30:1.

Suitable microfibers have a mean diameter between approximately 1 and 60 microns (μm) and a mean length between approximately 25 and 1000 μm. Preferred microfiber fillers or blends have a mean diameter between 0.1 and 60, more preferably, the mean diameter of the microfiber is between 1 and 40, and most preferably, the mean diameter of the microfiber is between 1 and 30. Preferred microfiber filers or blends have a mean length between 25 and 5,000, more preferably, the mean length of the microfiber is between 30 and 1,000, and most preferably, the mean length of the microfiber is between 30 and 500. The presently most preferred filer, Nyad G Wollastokup, is characterized primarily by mesh size. Ninety percent of this material passes through a 200 mesh screen (127×127 μm hole size). Visual observation of scanning electron microscope "SEM" photos indicates the average fiber diameter to be in the range of 10 to 30 μm and the average fiber length to be in the range of 200 to 400 μm.

The microfiber can be naturally occurring inorganic fibers, synthetic inorganic fibers, naturally occurring organic fibers, and synthetic organic fibers. The fiber, if inorganic, can be amorphous, single crystal (e,g., a whisker), polycrystalline, or multiphase. Blends of fibers can be employed if desired.

The various structural features of inorganic fibers reflect the complex interaction of fiber chemistry and fiber formation technique. Amorphous inorganic fibers such as fiberglass and fused silica fibers are manufactured by melt spinning. Although these fibers possess relatively high tensile strength, their modulus is among the lowest of inorganic fibers. On the other hand, single crystal fibers, sometimes referred to by those skilled in the an as "whiskers," are generally chemically pure and highly ordered. This results in strength approaching the theoretical limit, making them the strongest of all fibers.

Whiskers are the ultimate-strength short-fiber material. They are small (being submicron to several microns in diameter), single-crystal fibers with a high degree of crystalline perfection. In general, the smaller the whisker, the greater the perfection. This perfection results from low dislocation density, low void content, low internal and surface imperfections, and no grain boundaries. Whiskers typically have high mechanical properties: for example, a tensile strength between 13 GPa to 32 GPa (10 times that of most conventional fibers), a modulus of 450 GPa to 900 GPa, an elongation of 3 to 4 percent, and an exceptionally high degree of toughness and nonfriability.

Microfibers can be made relatively quickly by low-cost processing techniques, such as precipitation from a supersaturated solution, However, because they are made rapidly and from a liquid they do not possess the purity and crystalline perfection of a true whisker. These fibers are generally polycrystalline fiber bundles with grain boundaries and they often contain voids, dislocations, and crystalline imperfections rarely found in a true whisker. Nevertheless, such microfibers have, in general, much superior properties than the cured matrix resin which surrounds them and are suitable for use in the casting materials of the present invention.

Suitable inorganic microfibers include, for example, boron fibers, potassium titanate fibers, calcium sulfate fibers (e.g., Franklin Fiber), and processed mineral fibers such as asbestos (i.e., chrysotile or hydrated magnesium silicate), and wollastonite (i.e., calcium metasilicate—$CaSiO_3$). Asbestos, while suitable, is not preferred at the present time because of health considerations.

Suitable microfiber fillers of the present invention are incorporated into the liquid resin in an amount sufficient to provide the desired increased strength while not adversely affecting the uncured resin suspension viscosity. A suitable amount of a filler in a resin will result in a suspension having a viscosity prior to being cured of less than 500 Pa s as measured at 23° C. using a Brookfield RTV Rotovisco viscometer with either a #6 or #7 spindle (viscosities greater than 100 Pa s should be measured with the #7 spindle). Preferred suspensions have a viscosity prior to being cured of between about 5 and 100 Pa s, more preferably between about 10 and 70 Pa s and most preferably between about 30 and 70 Pa s. While the exact amount of microfiber filler can not be precisely determined owing to factors such as initial resin viscosity, microfiber type, microfiber size and aspect ratio, suitable suspensions for use in the present invention contain up to about 40 percent microfiber filler. Preferred suspensions of resin and microfiber filler contain between about 3 and 35 percent microfiber filler. More preferred suspensions of resin and microfiber filler contain between about 7 and 25 percent microfiber filler. Most preferred suspensions of resin and microfiber filler contain between about 10 and 25 percent microfiber filler.

If desired, the microfiber fillers may be surface treated using silanes, titanates, zirconates and the like to enhance resin bonding, ease of mixing, and compatibility. The surface treatment may be performed prior to incorporation of the microfiber into the resin or in-situ, i.e., the surface treatment agent may be incorporated into the suspension for later reaction with the filler.

Ring strength was measured as described in the following procedure. A cylindrical ring comprising 6 layers of the resin-coated material was formed by taking a roll of the resin-coated material from its storage pouch and immersing the roll completely in deionized water having a temperature of about 27° C. for about 30 seconds. The width of the ring formed was the same as the width of the resin-coated material employed, namely, 7.62 cm. The roll of resin-coated material was then removed from the water and the material was wrapped around a 5.08 cm diameter mandrel covered with a thin stockinet (such as 3M Synthetic Stockinet MS02) to form 6 complete uniform layers using a controlled wrapping tension of about 45 grams per centimeter width of material. Each cylinder was completely wound within 30 seconds after its removal from the water.

After 20 minutes from the initial immersion in water, the cured cylinder was removed from the mandrel, and after 24 hours from the initial immersion in water its strength was determined, i.e., samples were allowed to cure for 24 hours in a controlled atmosphere of 25° C.±2° C. and 55%±5% relative humidity prior to testing.

At the appropriate time each cylinder was then placed in a fixture in a commercial testing machine, e.g., an Inswon instrument, and compression loads were applied to the cylindrical ring sample along its exterior and parallel to its axis. The cylindrical ring was placed lengthwise between the two bottom bars of the fixture (the bars being 1.9 cm wide, 1.3 cm in height, and 15.2 cm long), with the bars spaced about 4 cm apart. The inside edges of the bars were machined to form a curved surface having a 0.31 cm radius. A third bar (0.63 cm wide, 2.5 cm high, and 15.2 cm long) was then centered over the top of the cylinder, also parallel to its axis. The bottom or contacting edge of the third bar was machined to form a curved surface having a 0.31 cm radius. The third bar was brought down to bear against and crush the cylinder at a speed of about 5 cm/min. The maximum of peak force which was applied while crushing the cylinder was then recorded as the "ring strength," which in this particular instance is the "dry strength" (expressed in terms of force per unit length of the cylinder, i.e., newtons/cm). For each material, at least 5 samples were tested, and the average peak force applied was then calculated and reported as the dry "ring strength."

One can determine the degree of extensibility a fabric or casting bandage possess using either an Instron test or a dead weight test on a "stretch table" as described below. A stretch table is constructed by having a pair of 15.25 cm wide clamps spaced exactly 25.4 cm apart. One clamp is stationary and the second clamp is movable on essentially frictionless linear roller bearings. Attached to the movable clamp is a cord secured to an appropriate weight. A stationary board is positioned on the base of the table with a measuring tape to indicate the lineal extension of the fabric when stretched in response to the gravitational force of the applied weight. Alternatively, an Instron model 1122 machine is set up with fabric clamps spaced exactly 25.4 cm apart. A fabric is placed in the fixtures and tested as indicated herein.

Tests are carried out at ambient temperature (e.g. 23°–25° C.) and at 50% relative humidity. The extensibility test is applicable to both resin coated and uncoated fabrics. Step 1: A piece of unstretched fabric is cut to approximately 30.5 cm. Markings are made on the fabric exactly 25.4 cm apart. If the fabric is coated with a curable resin this operation should be done in an inert atmosphere and the samples sealed until tested. For all samples it is necessary to take extreme care not to stretch the samples prior to testing. Step 2: The fabric is then secured in the test fixture under a very slight amount of tension (e.g. 0.0001 N/cm of bandage width) to ensure that the fabric is essentially wrinkle free. The length of the unstretched bandage should be 25.4 cm since the clamps are separated by this distance. If the 25.4 cm markings applied in the first step do not line up exactly with the clamp the fabric may have been stretched and should be discarded. In the case of a vertical test set up where the weight of the bandage (especially if resin coated) is sufficient to result in extension of the fabric the bandage should be secured in the clamps at exactly the marks made in step 1. Step 3: A weight is then attached to the clamp. Unless otherwise indicated, the weight should be 268 g/cm width of tape. Step 4: The sample is then extended by slowly and gently extending the fabric until the full weight is released. In cases where an Instron is used the sample is extended at a rate of 12.7 cm/min until the proper load has been reached. If the fabric being tested continues to stretch under the applied load the % stretch is taken 1 min after applying the load. Step 5: The % stretch is recorded as the amount of lineal extension divided by the original sample length and this value multiplied by 100. Note that testing of moisture curable resin coated fabrics must be performed rapidly in order to avoid having cure of the resin effect the results.

The following examples are offered to aid in understanding of the present invention and are not to be construed as limiting the scope thereof. Unless otherwise indicated, all parts and percentages are by weight.

EXAMPLES

Example 1

Bias Cut Sontara 8043 Microcreping

A roll of Sontara 8043 hydroentangled polyester nonwoven having the following properties, as set out below in Table 1a, was used as an input material for the microcreping process.

TABLE 1a

| Property | Measured Value |
| --- | --- |
| Basis weight | 70.0 g/m$^2$ |
| Thickness | 0.71 mm |
| Openings per square cm | 9.9 |
| Aperture size | 1.3 mm × 2.0 mm |
| Extensibility[1] | 3.4% in the machine direction |
| Extensibility | 48.0% in the cross direction |
| Average fiber bundle cross sectional area | 0.65 square mm |
| Average number of fibers per bundle | 417 |

[1]Extensibility was measured at a load of 0.26 Newtons per mm width.

The "jumbo" roll of fabric was unrolled and cut on the bias 30 degrees from the horizontal in 0.91 meter widths. The pieces were sewn together on a standard sewing machine and microcreped on a Micrex compactor having a 193 cm wide open width and equipped with a bladeless set up, i.e. no rigid retarder was used. The surface of the flexible frictional retarder was equipped with 600 grit wet or dry sand paper (available from 3M). The main roll was heated to a temperature of 135° C. and the dry fabric was passed through at a speed of approximately 4.87 meters per minute. The take-up roll was set at a speed 60% slower, i.e. 2.93 meters per minute, in order to ensure 40% compaction. A very uniform web was produced which had the following properties:

TABLE 1b

| Property | Microcreped Web | Input Web |
| --- | --- | --- |
| Basis weight (g/m$^2$) | 120 | 70 |
| Thickness (mm) | 0.86 | 0.71 |
| Openings per square cm | 16.7 | 9.9 |
| Extensibility[1] (%) machine | 87.5 | 36.3 |

[1] Extensibility was measured at a load of 0.26 Newtons per mm width.

The fabric was slit under minimal tension to 76.2 and 101.6 mm widths on a rotary knife score slitter. The fabric was found to exhibit some rebound, i.e. when stretched the fabric would recover. This indicates that the fabric fibers were annealed in the compacted condition. It is also interesting to note that the extensibility of the fabric increased dramatically upon microcreping while only slightly increasing in thickness. As can be seen from the above data, the percent stretch of the microcreped fabric in the machine direction is more than double the input material's extensibility in the machine direction. At the same time the microcreped web experienced only a 21% increase in web thickness. This suggests that much of the compacting is occurring in the plane of the fabric, i.e. the fiber bundles are being crimped into the aperture spaces.

A 3.8 liter (one gallon) glass vessel equipped with a 12.7 cm×2.54 cm×0.318 cm Teflon™ impeller, addition funnel, nitrogen purge line, and thermometer was assembled and purged with nitrogen for 30 minutes to ensure that the entire apparatus was completely dry. The following chemicals were added to the reactor through the addition funnel in order and at 5 minute intervals:

TABLE 1c

| Chemical | Equivalent weight[3] | Weight (%) |
| --- | --- | --- |
| Isonate 2143L (Dow Chemical Co.) | 144.3 | 56.9 |
| Mesitylenesulfonyl chloride | | 0.05 |
| Antifoam 1400 (Dow Chemical) | | 0.18 |
| Butylated hydroxytoluene ("BHT") | | 0.48 |
| Pluronic F-108 (BASF) | 7250 | 5.00 |
| MEMPE[1] | | 1.00 |
| Arcol PPG-2025 (Arco) | 1016.7 | 22.3 |
| Arcol LG-650 (Arco) | 86.1 | 5.60 |
| Niax E-562[2] | 1781 | 8.50 |

[1]"MEMPE" = Morpholinoethylmorpholinoisopropyl ether.
[2]"E-562" = Polymer filled polyol (formerly available from the Union Carbide Corp. and now available from Arco as Arcol Polyol 24–32).
[3]The combined ingredients provide an NCO to OH ratio of 4.25 and NCO equivalent weight of 331.5 g/equivalent.

The agitation rate was gradually increased as the viscosity increased. The vessel was temporarily insulated with glass wool, gently heated with a heating mantle, and the temperature of the reaction was allowed to increase to 65° C. and held at that temperature for 1.5 hours. The glass wool was removed along with the agitator, thermometer, and addition funnel. The vessel was sealed and the resin was allowed to cool for 24 hours.

After this time, 20 parts Nyad G Wollastokup 10012 (available from Nyco, Willsboro, N.Y.) microfiber filer was added to 80 parts resin to yield a composition having 20% by weight microfiber filer. The resin was sealed inside a jar and allowed to cool overnight while rotating on a roller at about 7 revolutions per minute (rpm). This filed resin composition was then coated on the above described fabric at a coating weight of 4.2 grams filled resin per 1 gram fabric (i.e., approximately 3.24 grams resin, on a filer free basis, per gram fabric). The coating was performed by spreading the resin directly on one surface and while the fabric was under minimal tension. The coated fabric was then convened into 3.35 m rolls wrapped around a 1.2 cm diameter polyethylene core. The converting operation was also done under minimal tension to avoid stretching the fabric. The rolls were then placed into aluminum foil laminate pouches for later evaluation.

The material was evaluated by: (1) removing the roll from the pouch; (2) dipping the roll under 23°–25° C. water while squeezing three times, followed by a final squeeze to remove excess water; and (3) wrapping the bandage on a forearm. The material was found to be very conformable and easy to mold compared to a non-microcreped sample. Note that when the tape was immersed in water it quickly became very slippery. The roll unwound easily and did not stick to the gloves of the applier. Molding was easy due to the non-tacky nature of the resin. The cast was rubbed over its entire length without sticking to the gloves, yet the layers bound well to each other. The final cured cast had a much smoother finish than typical fiberglass casting materials, and could be drawn on and decorated with felt tip marker much more easily and legibly than fiberglass casting materials. The material was also found to be much more palpable than typical fiberglass casting tapes. The cast quickly became very strong (i.e., within 20–30 minutes) and had a very pleasing appearance. Additional rolls of casting tape were then evaluated for strength using the dry ring strength procedure described previously. The cured material had an average dry ring strength of 72.1 N/cm width (average of 7 samples).

EXAMPLE 2

Machine Direction Sontara 8043 Microcreping

A Sontara 8043 hydroentangled polyester nonwoven as described in Example 1 was sewn together on a standard sewing machine to form a single long sample. In contrast to the fabric of Example 1, the fabric of Example 2 was not cut on the bias but was cut across the machine direction and spliced together. The fabric was then microcreped on a Micrex compactor having a 193 cm wide open width and equipped with a bladeless set up, i.e. no rigid retarder was used. The surface of the flexible frictional retarder was equipped with 600 grit wet or dry sand paper (available from 3M). The main roll was heated to a temperature of 135° C. and the dry fabric was passed through at a speed of approximately 4.87 meters per minute. The take-up roll was set at a speed 70% slower, i.e. 3.41 meters per minute in order to ensure 30% compaction. This web is referred to as #2-30. The above process was repeated except that the web was compacted 40% using a take up speed of approximately 2.93 meters per minute. This web is referred to below as #2-40. At these compaction rates very uniform webs were produced which had the following properties:

TABLE 2a

| Property | # 2–30 | # 2–40 | Input |
|---|---|---|---|
| Basis weight (g/m²) | 120 | 118 | 70 |
| Thickness (mm) | 0.99 | 0.97 | 0.71 |
| Openings per square cm | 15.6 | 20.0 | 9.9 |
| Extensibility[1] (%) machine direction | 35.5 | 58.3 | 3.4 |

[1]Extensibility was measured at a load of 0.26 Newtons per mm width.

The fabric was slit under minimal tension to 76.2 and 101.6 mm widths on a rotary knife score slitter. The fabric was found to exhibit some rebound, i.e. when stretched the fabric would recover. This indicates that the web was annealed in the compacted condition. It is also interesting to note that the extensibility of the fabric increased dramatically upon microcreping while only slightly increasing in thickness. As can be seen from the above data, the percent stretch of the microcreped fabric in the machine direction is more than ten times the input material's extensibility in the machine direction. At the same time the microcreped web experienced only a 38% increase in web thickness. This suggests that much of the compacting is occurring in the plane of the fabric, i.e. the fiber bundles are being crimped into the aperture spaces.

The slit rolls were then coated, as previously described in Example 1, with the resin described in Example 1. The material was evaluated by: (1) removing the roll from the pouch; (2) dipping the roll under 23°–25° C. water while squeezing three times, followed by a final squeeze to remove excess water, and (3) wrapping the bandage on a forearm. The material was found to be very conformable and easy to mold compared to a non-microcreped sample. The material was also found to be much more palpable than typical fiberglass casting tapes, with the 40% compacted material (#2-40) being more conformable than the 30% compacted material (#2-30). Neither bandage was quite as conformable as the bandage of Example 1.

Additional rolls of casting tape were then evaluated for strength using the dry ring strength procedure described previously. The cured materials had an average dry ring strength of 89.7 N/cm width (#2-30) and 90.4 N/cm width (#2-40).

EXAMPLE 3

Microcreped Knit

A polyester knit was produced using a microdenier polyester yarn according to the following specifications:

Micromatique Polyester (available from DuPont and texturized by Unifi Inc, Greensboro, N.C.) Single yarn, 150 denier, 200 filament (1/150/200). The fabric was knit using a Rashchelina RB Crochet type warp knitting machine from the J. Muller Co. This machine was equipped with a 6 gauge (6 needles/cm) needle bed.

The knit produced was microcreped according to the procedure of Example 1. The microcreped fabric was found to have rebound, i.e. when stretched the fabric would recover. This indicates that the fibers had been annealed in the compacted condition. The properties of the fabric before and after microcreping are shown below in Table 3a.

TABLE 3a

| Property | Input Fabric | Output Fabric (Microcreped) |
|---|---|---|
| Wales per cm | 7.5 | 7.5 |
| Stitches per cm | 7.9 | 11.8 |
| Basis weight (g/m²) | 124 | 167 |
| Thickness (mm) | 0.76 | 0.84 |
| Openings per square cm | 59 | 87.9 |
| Extensibility % in the machine direction | 15 | 55.9 |

It is also interesting to note that the extensibility of the fabric increased dramatically upon microcreping while only slightly increasing in thickness. This indicates that much of the compacting is occurring in the plane of the fabric, i.e. the apertures are being distorted.

Various modifications and alterations of this invention will be apparent to those skilled in the art without departing from the scope and spirit of this invention, and it should be understood that this invention is not limited to the illustrative embodiments set forth herein.

What is claimed is:
1. An article, comprising:
 a microcreped fibrous fabric sheet; and
 a curable liquid resin coated onto said fabric sheet, wherein said article further comprises a microfiber filler associated with said resin, wherein said microfiber filler has an aspect ratio between about 5:1 and 200:1.

2. An article, as defined in claim 1, wherein said sheet comprises a fiber selected from the group consisting of: natural organic fibers; animal derived materials; naturally based organic polymer fibers; and synthetic polymer fibers.

3. An article, as defined in claim 2, wherein said sheet has from about 25% to about 75% extensibility in the elongated direction when a 268 gram load or force is applied across a 1 cm section of the fabric.

4. An article, as defined in claim 3, wherein said curable resin is a water-curable resin comprising a water-reactive liquid organometallic compound and an organic polymer.

5. An article, as defined in claim 3, wherein said curable resin is a water-curable resin comprising isocyanate-functional prepolymers.

6. An article, as defined in claim 3, wherein said fabric has between about 6 and 90 openings persquare cm.

7. An article, according to claim 6, wherein said resin has a viscosity between about 10 Pa s and 100 Pa s.

8. An article, as defined in claim 1, wherein said sheet comprises a fiber selected from the group consisting of: cotton, wool, acrylic, nylon, polyethylene, polypropylene, polyester, and rayon.

9. An article, as defined in claim 8, wherein said sheet has from about 35% to about 55% extensibility in the elongated direction when a 268 gram load or force is applied across a 1 cm section of the fabric.

10. An article, as defined in claim 1, wherein said fabric was compacted to between about 10 and 65 percent of its original dimension in the lengthwise direction.

11. An article, as defined in claim 1, wherein said fabric was compacted to between about 20 and 50 percent of its original dimension in the lengthwise direction.

12. An article, as defined in claim 1, wherein said article is selected from the group consisting of orthopedic casts, orthopedic splints, braces, supports, protective shields, and orthotics.

13. An article, as defined in claim 1, wherein said article is in the form of an orthopedic casting bandage, wherein said casting bandage has from about 35% to about 65% extensibility in the elongated direction when a 268 gram load or force is applied across a 1 cm section of the fabric sheet.

14. An orthopedic casting bandage, as defined in claim 13, wherein said casting bandage further comprises: between 3 and 35 percent of a microfiber filler associated with said resin, wherein said microfiber filler has an aspect ratio between about 5:1 and 200:1, and wherein said fabric sheet has between about 6 and 70 openings per square cm.

15. An orthopedic casting bandage, comprising a fabric sheet and a curable liquid resin coated onto said fabric sheet, wherein said fabric sheet is treated to a mechanical compaction process so as to mechanically crimp said fibers of said fabric sheet thereby producing a compacted fabric sheet, and wherein said compacted fabric sheet is coated with a sufficient amount of a curable liquid resin so as to provide an orthopedic casting material having sufficient strength to immobilize a body part, wherein said casting bandage has from about 35% to about 65% extensibility in the elongated direction when a 268 gram load or force is applied across a 1 cm section of the fabric sheet.

16. An orthopedic casting bandage, as defined in claim 15, wherein said mechanical compaction process comprises the steps of:

supporting an untreated fabric by a main roll;

introducing said supported fabric into a converging passage between said main roll and a movable retarder comprising a flexible retarder; and introducing said fabric through a secondary passage between said flexible retarder and a rigid retarder, to thereby compact said fabric and, wherein said fabric sheet was thereby compacted to between about 10 and 65 percent of its original dimension.

17. An orthopedic casting bandage, as defined in claim 15, wherein said mechanical compaction process comprises the steps of:

supporting an untreated fabric by a main roll;

introducing said supported fabric into a converging passage between said main roll and a movable retarder comprising a primary surface, a flexible retarder and a frictional retarder; and introducing said fabric through a secondary passage between said frictional retarder and said main roll, to thereby compact said fabric, and wherein said fabric sheet was compacted to between about 10 and 65 percent of its original dimension.

18. An orthopedic casting bandage, as defined in claim 15, wherein said mechanical compaction process comprises the steps of:

supporting an untreated fabric by a main roll;

introducing said supported fabric into a converging passage between said main roll and a movable retarder comprising a primary surface, a flexible retarder and at least one back-up blade; and introducing said fabric through a secondary passage between said flexible retarder and a comb, to thereby compact said fabric, and wherein said fabric sheet was compacted to between about 10 and 65 percent of its original dimension.

19. An orthopedic casting bandage, as defined in claim 15, wherein said mechanical compaction process comprises the steps of:

supporting an untreated fabric by a feed roll;

introducing said supported fabric into a passage between said feed roll and an upper compacting shoe; and introducing said fabric through a secondary passage between said upper compacting shoe and a lower compacting shoe, to thereby compact said fabric, and wherein said fabric sheet was compacted to between about 10 and 65 percent of its original dimension.

\* \* \* \* \*

UNITED STATES PATENT AND TRADEMARK OFFICE
CERTIFICATE OF CORRECTION

PATENT NO.: 5,498,232

DATED: March 12, 1996

INVENTOR(S): Matthew T. Scholz

It is certified that error appears in the above-identified patent and that said Letters Patent is hereby corrected as shown below:

Col. 1, line 23, "wright" should read -- weight --.

Col. 1, line 33, "an" should read -- art --.

Col. 3, line 8, "pan" should read -- part --.

Col. 3, line 16, "an" should read -- art --.

Col. 3, line 22, "an" should read -- art --.

Col. 7, line 59, "east" should read -- cast --.

Col. 9, line 37, "an" should read -- art --.

Col. 12, line 32, "filers" should read -- fillers --.

Col. 14, line 11, "Inswon" should read -- Instron --.

Col. 16, line 49, "filer" should read -- filler --.

Col. 16, line 51, "filer" should read -- filler --.

Col. 16, line 53, "filer" should read -- filler --.

Col. 16, line 56, "filer" should read -- filler --.

UNITED STATES PATENT AND TRADEMARK OFFICE
CERTIFICATE OF CORRECTION

PATENT NO. : 5,498,232

DATED : March 12, 1996

INVENTOR(S) : Matthew T. Scholz

It is certified that error appears in the above-identified patent and that said Letters Patent is hereby corrected as shown below:

Col. 16, line 59, "convened" should read -- converted --.

Signed and Sealed this

Sixteenth Day of June, 1998

Attest:

BRUCE LEHMAN

*Attesting Officer*     *Commissioner of Patents and Trademarks*